United States Patent
Biallas et al.

(10) Patent No.: US 6,628,393 B1
(45) Date of Patent: Sep. 30, 2003

(54) METHOD FOR DETERMINING THE SHADE STABILITY OF LACQUERS

(75) Inventors: Bernd Biallas, Albersloh (DE); Wolfgang Duschek, Münster (DE); Werner Rotz, Münster (DE); Harald Berlin, Nottuln (DE)

(73) Assignee: BASF Coatings AG, Muenster-Hiltrup (DE)

( * ) Notice: Subject to any disclaimer, the term of this patent is extended or adjusted under 35 U.S.C. 154(b) by 0 days.

(21) Appl. No.: 09/744,639

(22) PCT Filed: Jun. 30, 1999

(86) PCT No.: PCT/EP99/04496

§ 371 (c)(1),
(2), (4) Date: May 15, 2001

(87) PCT Pub. No.: WO00/07009

PCT Pub. Date: Feb. 10, 2000

(30) Foreign Application Priority Data

Jul. 28, 1998 (DE) .......................... 198 33 859

(51) Int. Cl.[7] .................... G01J 3/46; G01N 33/32
(52) U.S. Cl. ........................ 356/402; 356/405
(58) Field of Search ................ 356/402, 405; 73/53.01

(56) References Cited

U.S. PATENT DOCUMENTS

| | | | | |
|---|---|---|---|---|
| 3,690,771 A | * | 9/1972 | Armstrong et al. | 356/405 |
| 5,231,472 A | * | 7/1993 | Marcus et al. | 356/402 |
| 5,583,642 A | | 12/1996 | Nakazono | 356/405 |
| 5,933,243 A | * | 8/1999 | Hagen | 356/402 |
| 5,963,334 A | * | 10/1999 | Yamaguchi et al. | 356/425 |
| 6,261,631 B1 | * | 7/2001 | Lomasney et al. | 427/9 |

FOREIGN PATENT DOCUMENTS

| | | | |
|---|---|---|---|
| DE | 196 05 520 C | 4/1997 | G01B/11/30 |
| DE | 197 54 547 A1 | 12/1997 | G01B/11/30 |
| DE | 197 09 406 A1 | 4/1998 | C05D/21/02 |
| EP | WO98/14778 A | 4/1998 | G01N/33/32 |

* cited by examiner

Primary Examiner—F. L. Evans
Assistant Examiner—Kara Geisel

(57) ABSTRACT

In a method of determining the shade stability of paints, the total color difference $\Delta E(FT)$ between the color at the film thickness FT and the color at a predetermined film thickness $FT_0$ is measured for different film thicknesses FT. Subsequently, the slope $\sigma(FT)$ of the plot $\Delta E(FT)$ is determined, which represents a useful parameter for the shade stability. Alternatively to $\sigma(FT)$, it is also possible to determine the limiting film thickness $FT_{lim}$ at which the total color difference $\Delta E(FT)$ passes below a predetermined limit. The method of determining the shade stability is additionally employed in order to optimize paint formulations.

14 Claims, 1 Drawing Sheet

METHOD FOR DETERMINING THE SHADE STABILITY OF LACQUERS

This application claims priority under 35 U.S.C. Sec. 120 upon International PCT Application PCT/EP99/04496 and German Patent Application DE 198 33 859.7, filed Jul. 28, 1998.

The present invention relates to a method of determining the shade stability of coating materials and of optimizing a paint formulation in respect of the shade stability.

When paints and other coating compositions are used for industrial coating it is important to observe a shade, once predetermined, or a shade desired by the customer, with the maximum possible accuracy and uniformity, since even the slightest deviations in color are evident to the human eye. It is necessary in particular to ensure that color deviations arising through different film thicknesses of the coating do not reach an intolerable magnitude.

The assessment of a paint is based substantially on the physiological fact that the human eye contains three kinds of receptors having different spectral sensitivities, which roughly speaking can be assigned to the three primary colors red, green and blue (cf. Glasurit-Handbuch Lacke und Farben, Vincentz Verlag Hannover 1984, 11$^{th}$ edition, page 220ff.). In order to be able to determine objective data, statistical averaging has been used to specify standard distribution coefficients $x(\lambda)$, $y(\lambda)$ and $z(\lambda)$ for the three sensitivities of the receptors (CIE system, DIN 5033). By integrating an arbitrary color spectrum $f(\lambda)$ with these standard distribution coefficients it is possible to obtain what are known as the tristimulus values $X=\int d\lambda x(\lambda)f(\lambda)$, $Y=\int d\lambda y(\lambda)f(\lambda)$, $Z=\int d\lambda z(\lambda)f(\lambda)$, which represent objective values for characterizing the color spectrum f and may be illustrated as the extent of stimulation of the three types of receptor in the eye.

In order better to harmonize the above-described chromaticity coordinate system with human sensation in respect of the distance between two colors $X_1,Y_1,Z_1$ and $X_2,Y_2,Z_2$, moreover, the variables $L^*,a^*,b^*$ were defined in the CIELAB system (DIN 6174) as follows ($X_n,Y_n,Z_n$ are the coordinates of the standardized light used for the illumination):

$$L^*=116(Y/Y_n)^{1/3}-16$$

$$a^*=500[(X/X_n)^{1/3}-(Y/Y_n)^{1/3}]$$

$$b^*=200[(Y/Y_n)^{1/3}-(Z/Z_n)^{1/3}]$$

The total color difference $\Delta E^*$ between the two colors is then given, in the $L^*$-$a^*$-$b^*$ system, by the Euclidean difference $$\Delta E^*=[(\Delta L^*)^2+(\Delta a^*)^2+(\Delta b^*)^2]^{1/2}$$

When the shade behavior of a coating material is to be assessed in practice, then, in accordance with the present state of the art (for example, in a method according to DE 196 40 376.6), sample coatings are measured visually or by colorimetry in order to determine, for example, the values $L^*,a^*,b^*$ for different film thicknesses of the coating and different observation angles. This produces a large volume of data, difficult to comprehend, from which it is necessary to estimate whether the coating material investigated has a sufficient constancy of shade in its area of application. In particular, fluctuations in the film thickness of the coating on, for example, an automobile body, which occur automatically in practice, must not lead to an obvious change in the shade. The above-described estimation of the coating material on the basis of the large volume of data from the sample measurements is of course extremely difficult and requires much effort and experience in evaluation. In any case, the result is highly subjective and dependent on the abilities of the assessor.

It is therefore an object of the present invention to avoid these disadvantages and to develop a method of determining the shade stability of the coating materials which provides a useful, comprehensible and objective measure which also correlates well with the findings from a painting line. The intention is also to specify a method of optimizing paint formulations with regard to the shade stability.

This object is achieved by means of a method of determining the shade stability of coating materials, comprising a first step of a) measuring, for different film thicknesses FT, the total color difference $\Delta X=\Delta X(FT)$ between the color at the respective film thickness FT and the color at a predetermined film thickness $FT_0$.

Accordingly, the color coordinates of the coating are first of all determined at a reference film thickness $FT_0$. This reference film thickness $FT_0$ is preferably chosen so as to lie at the edge of the film thickness fluctuations which occur in practice. If, for example, fluctuations between 10 and 20 $\mu$m are to be expected, $FT_0=20$ $\mu$m (or even $FT_0=25$ $\mu$m) would therefore be an appropriate choice. The color coordinates are then determined likewise for other film thicknesses FT; the number of film thicknesses measured must be determined individually, balancing the effort of the measurement against the desired accuracy of the result. The range of the film thicknesses measured will substantially overlap with the range of the film thickness fluctuations which occur in the course of production line painting (above example: 10–20 $\mu$m). Using the color coordinates for the film thicknesses FT, it is then possible to define a total color difference $\Delta X(FT)$ in relation to the color coordinates of the reference film thickness $FT_0$. If the color coordinates are expressed, for example, in the $L^*$-$a^*$-$b^*$ system, $\Delta X$ may be chosen in agreement with the known definition $$\Delta X=\Delta E^*:=[(\Delta L^*)^2+(\Delta a^*)^2+(\Delta b^*)^2]^{1/2}.$$

However, it should be pointed out expressly that this is only one of several possible choices. With $L^*$-$a^*$-$b^*$ values it would also be possible, for example, to use the variables $$\Delta X\,\Delta C^*:=[a^{*2}+b^{*2}]^{1/2}-[a_0^{*2}+b_0^{*2}]^{1/2}$$

or $$\Delta X\,\Delta H^*:=[(\Delta E^*)^2-(\Delta L^*)^2-(\Delta C^*)^2]^{1/2}.$$

The results obtained from component step a) of the method of the invention is therefore the film thickness dependency of the total color difference $\Delta X(FT)$ (i.e., the difference between the color at the film thickness FT and the color at the reference film thickness $FT_0$).

Then, in the second step of the method of the invention, b) the slopes $$\sigma(FT)=d\Delta X/dFT$$

are determined as parameters for the shade stability at the film thickness FT.

Accordingly, the slope $\sigma(FT)$ at the film thickness FT is the derivation of the total color difference $\Delta X$ in accordance with the film thickness FT. This slope indicates how strongly the color at the film thickness FT depends on the change in film thickness.

Surprisingly it has been found that the parameter σ(FT) thus determined is particularly informative in respect of the shade stability of the coating material. A particular advantage in this context is that it bundles three color coordinates (e.g., L*,a*,b*) into a single value. The assessment of shade stability is therefore no longer left to the experience or the feeling of the evaluator but instead can be made on the basis of an objectively and reproducibly determinable parameter.

The method of the invention may preferably be implemented by measuring the color coordinates L*,a*,b* directly using an appropriate apparatus and calculating from these measurements the total color difference ΔX.

The measurement of the total color difference ΔX and/or of the coordinates L*,a*,b* may be performed under various observation angles between 0° and 180°, preferably at 15°, 25°, 45°, 75°, and 110°. This procedure is necessary when the perceived color of a coating is dependent on the direction of observation and/or of illumination. The latter is the case with many coatings, especially the coatings known as effect coatings.

In the cases of angle dependency it has been found that from the $\Delta X_\alpha$ it is possible to form a (preferably geometric) average value $\Delta X_{total}$ which, without detracting from the informativeness of the individual values, indicates the shade stability. On the basis of this value $\Delta X_{total}$ it is possible to determine the slope $\sigma_{total}$ (FT).

An alternative concept is to average the parameters $\sigma_\alpha$(FT) in respect of the observation angles α. A very sensitive parameter $\sigma_{max(\alpha)}$ (FT) is given, moreover, when the maximum of σ over all observation angles is formed.

A further possibility is not to evaluate the parameters σ(FT) separately for all film thicknesses FT. Here again, it is conceivable to average the parameters over the film thickness range that is of interest, in order to obtain, accordingly, the average value <σ>. As an alternative to the averaging, however, it would also be possible to consider the maximum $\sigma_{max(FT)}$ of σ over all film thicknesses FT within the range. Both methods provide as their result a single number as a characteristic of the shade stability of the coating.

These advantages as depicted above may also be obtained by determining in step b) not the parameter σ(FT) but rather b') the limiting film thickness $FT_{lim}$ at which the total color difference ΔX(FT) passes below a preset limit $\Delta X_0$, as parameter for the shade stability of the coating.

In this method, the film thickness dependency of the parameter is absent from the outset, and a single characteristic numerical value $FT_{lim}$ is obtained. This value provides illustrative information on whether a shade-stable behavior exists in the region of the process film thickness which is customary in practice. If, for example, the process film thickness customary in practice is situated in the range from 12 to 15 μm, then $FT_{lim}$ should be <12 μm.

In practice, the limit $\Delta X_0$ is chosen so that, within its boundaries, color deviations on a coated article would still just be tolerable. If, accordingly, industrial coating gives rise to expectations of film thickness fluctuations in a range $[FT_{min}, FT_{max}]$, then, for example, $FT_0$ will be chosen as equal to $FT_{max}$ and the shade stability of the coating will be considered adequate if the value $FT_{lim}$ resulting in the method of the invention is <$FT_{min}$.

The second method of the invention, comprising step b'), may preferably be implemented by measuring the color coordinates L*,a*,b* directly using an appropriate apparatus and calculating from the measurements the total color difference ΔX.

The measurement of the total color difference ΔX and/or of the coordinates L*,a*,b* may be performed at various observation angles between 0° and 180°, preferably at 15°, 25°, 45°, 75°, and 110°. This procedure is necessary when the perceived color of a coating is dependent on the direction of observation and/or of illumination. This is the case with many coatings, especially the coatings known as effect coatings.

In the cases of angle dependency it is conceivable to average the limiting film thicknesses $FT_{lim,\alpha}$ in respect of the observation angles α. It has, however, been found that the highest value $FT_{lim,\alpha}$ (i.e., that situated closest to $FT_0$) can be regarded as a variable which is characteristic of the stability. In other words, it indicates the film thickness which must be exceeded in the process in order to ensure shade stability.

The invention additionally provides a method of optimizing a paint formulation in respect of the shade stability within a film thickness range $[FT_{min}, FT_{max}]$.

In the development of new paint formulations for the OEM finishing of automobiles, for example, there are numerous requirements to be observed. One of them is that, within the film thickness range in which the finish is applied in practice, there are no obvious and disruptive fluctuations in the shade dependent on the film thickness. It is therefore necessary, if appropriate, to alter (optimize) a paint formulation until it has an adequate shade stability. Such optimization is possible in a simplified way with the method of the invention. This method comprises a) preparing at least two variants of the paint formulation, b) determining for each variant the parameters σ(FT) of the shade stability in the film thickness range $[FT_{min}, FT_{max}]$ by a method as described above, and c) choosing as the final paint formulation the variant which c1) has the smallest value σ(FT) in the film thickness range $[FT_{min}, FT_{max}]$, or c2) the smallest average <σ> over the film thickness range $[FT_{min}, FT_{max}]$, or c3) the smallest maximum value $\sigma_{max(FT)}$ in the film thickness range $[FT_{min}, FT_{max}]$.

The optimization method of the invention permits optimization of a paint formulation in a simple, reproducible and automatable way. A particular reason for its success is that it uses only a single variable σ, which may be used directly as an optimization criterion (target variable or cost function).

Provided the parameter σ has been defined as described above directly as the film thickness average or as the maximum value over a film thickness range, there is direct simplification of the steps c2) and c3) for the selection of the paint formulation having the minimal σ.

The paint formulations may be varied by minimizing the parameter σ in accordance with a gradient technique with changes in the paint formulation.

The optimization method of the invention is preferably carried out until the value σ used in accordance with c1), c2) or c3) is less than 0.15 $\mu m^{-1}$, preferably less than 0.1 $\mu m^{-1}$, in this case σ being determined specifically by way of the total color difference ΔE* in the L*-a*-b* system. For other definitions of σ, it is possible to determine corresponding predetermined values.

Of course, further modifications of the optimization method of the invention are conceivable. In particular it is also possible to implement it with the limiting film thickness $FT_{lim}$ as the measure of optimization; in other words, the paint formulation sought or chosen is that which has the better values of $FT_{lim}$. The criterion for discontinuing the optimization in this case would be the attainment of a paint whose $FT_{lim}$ leads to coverage of the entire film thickness range that is of interest.

The present invention is elucidated below by way of example with the aid of the figures.

In the figures, the film thickness FT between the values of 0 and 25 μm is plotted on the horizontal axis. For industrial coatings, it is approximately the range between 10 and 20 μm which is of interest.

On the vertical axis the total color difference $\Delta E(FT)$ is plotted, which in the examples corresponds to the value $$\Delta E^* = [(\Delta L^*)^2 + (\Delta a^*)^2 + (\Delta b^*)^2]^{1/2}$$

defined in the L*-a*-b* system. The color difference is related to the color at the film thickness $FT_0$, so that the color difference curve has a zero point at $FT_0$.

A predetermined limit $\Delta E_0 = 1$ is exceeded at the film thickness $FT_{lim}$. Above $FT_{lim}$, therefore, the coating would still be regarded as sufficiently stable in shade.

Furthermore, the slope σ of the tangent (drawn in by way of example for one point) to the $\Delta E^*$ plot represents a parameter in accordance with the invention for the shade stability. If this slope exceeds a predetermined value in the range that is of interest, the paint is not sufficiently stable in shade and cannot be processed with sufficient reliability. It has been found that σ should be less than 0.15 $\mu m^{-1}$.

Figure 1:
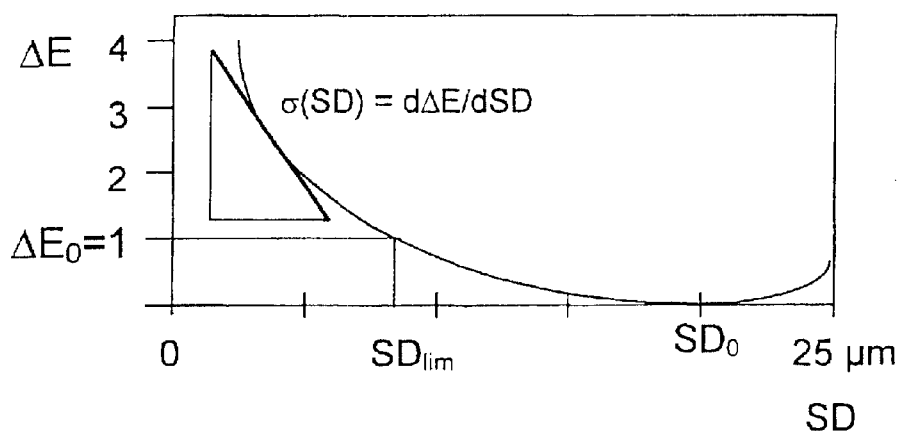
FIG. 1 shows a schematicized plot of the total color difference $\Delta E^*(FT)$.
Figure 2:
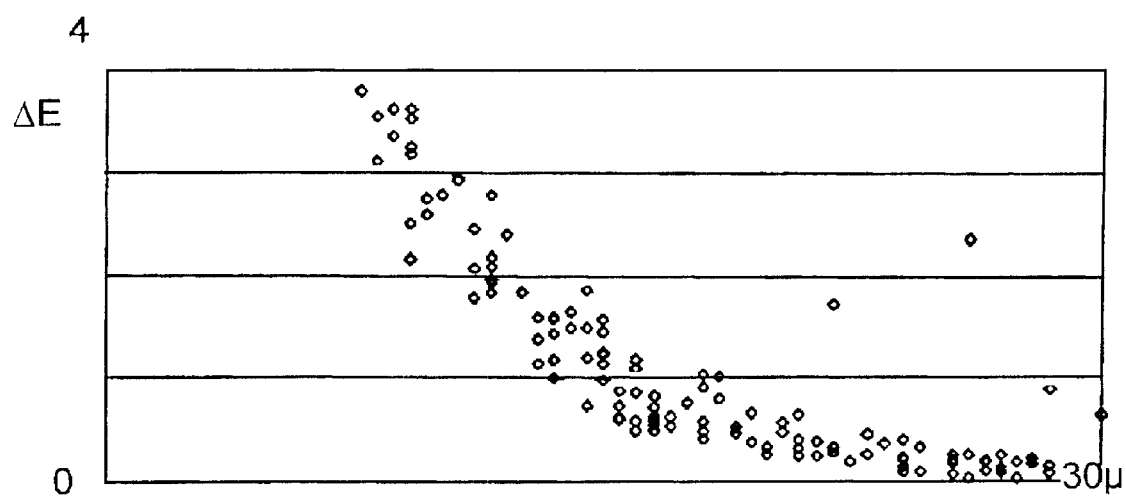
FIG. 2 shows a plot which is a result of measurement.

FIG. 2 shows the same diagram with values measured for basecoats which are used in automotive finishing. With a view to good correlation of the laboratory values obtained with the results in actual service on the painting line, it must be ensured that in the measurement procedure the basecoat in question is applied to the appropriate primer-surfacer.

What is claimed is:

1. A method of determining shade stability of coatings comprising
    a) measuring at different film thicknesses FT, a total color difference $\Delta X(FT)$ between a color at the film thickness FT and a color at a predetermined film thickness $FT_0$, and
    b) determining the slopes $\sigma(FT) = d\Delta X/dFT$ as parameters for the shade stability at the film thickness FT.

2. The method of claim 1, wherein color coordinates L*,a*,b* are measured directly and from these measurements the total color difference $\Delta X$ is calculated.

3. The method of claim 1 wherein the total color differences $\Delta X$ and/or the color values L*,a*,b* are measured at different observation angles.

4. The method of claim 3, wherein the total color difference for a given observation angle is given by $\Delta X_\alpha$, and the values $\Delta X_\alpha$ for each observation angle are averaged to give $\Delta X_{total}$, and from the resulting function $\Delta X_{total}(FT)$ a parameter $\sigma_{total}(FT)$ is calculated.

5. The method of claim 4, wherein the parameters $\sigma(FT)$ are averaged over a film thickness range to give a value $<\sigma>$.

6. The method of claim 3 wherein the different observation angles are selected from the group consisting of 15°, 25°, 45°, 75°, and 110°.

7. The method of claim 4, wherein a maximum value $\sigma_{max(FT)}$ of $\sigma(FT)$ is determined in a film thickness range.

8. A method of determining shade stability of coating materials comprising
    a) measuring at different film thicknesses FT, a total color difference $\Delta X(FT)$ between a color at the film thickness FT and a color at a predetermined film thickness $FT_0$, and
    b) determining a limiting film thickness $FT_{lim}$, at which the total color difference $\Delta X(FT)$ passes below a preset limit $\Delta X_0$, as parameter for the shade stability of the coating.

9. The method of claim 8, wherein the color coordinates L*,a*,b* are measured directly and from these measurements the total color difference $\Delta X$ is calculated.

10. The method of claim 8, wherein the total color differences $\Delta X$ and/or the color values L*,a*,b* are measured at different observation angles.

11. The method of claim 10, wherein a maximum value of the limiting film thicknesses $FT_{lim,\alpha}$ is determined as a parameter for the shade stability.

12. The method of claim 10 wherein the different observation angles are selected from the group consisting of 15°, 25°, 45°, 75°, and 110°.

13. A method of optimizing a paint formulation in respect of a shade stability in a film thickness range comprising
    a) preparing at least two variants of the paint formulation,
    b) determining for each variant a parameter $\sigma(FT)$ of the shade stability in the film thickness range by the method of claim 1, and
    c) choosing as the final paint formulation the variant which
       c1) has the smallest value σ in the film thickness range, or
       c2) the smallest average $<\sigma>$ over the film thickness range, or
       c3) the smallest maximum value $\sigma_{max(FT)}$ in the film thickness range.

14. The method of claim 13, wherein the optimization is implemented until the smallest value σ in the film thickness range is less than 0.15 $\mu m^{-1}$, σ being determined by way of the total color difference $\Delta E^*$ in a L*-a*-b* system.

* * * * *